United States Patent
Kimura et al.

(10) Patent No.: US 9,000,126 B2
(45) Date of Patent: Apr. 7, 2015

(54) CRYSTALLINE OXIDIZED GLUTATHIONE AND PRODUCTION METHOD THEREFOR

(75) Inventors: Ken Kimura, Hofu (JP); Kenta Fukumoto, Hofu (JP); Hiroshi Tanaka, Hofu (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 118 days.

(21) Appl. No.: 13/642,356

(22) PCT Filed: Apr. 21, 2011

(86) PCT No.: PCT/JP2011/059776
§ 371 (c)(1),
(2), (4) Date: Oct. 19, 2012

(87) PCT Pub. No.: WO2011/132724
PCT Pub. Date: Oct. 27, 2011

(65) Prior Publication Data
US 2013/0035470 A1    Feb. 7, 2013

(30) Foreign Application Priority Data

Apr. 21, 2010    (JP) ................... 2010-097529

(51) Int. Cl.
*C07K 5/08*    (2006.01)
*C07K 5/02*    (2006.01)
(52) U.S. Cl.
CPC .................... *C07K 5/0215* (2013.01)
(58) Field of Classification Search
CPC .................................................. C07K 5/0215
See application file for complete search history.

(56) References Cited

U.S. PATENT DOCUMENTS

| | | | |
|---|---|---|---|
| 8,188,308 B2 | 5/2012 | Shimose et al. | |
| 2004/0250751 A1 | 12/2004 | Shimose et al. | |

FOREIGN PATENT DOCUMENTS

| | | | |
|---|---|---|---|
| EP | 1 447 409 A1 | 8/2004 | |
| JP | 05-146279 A | 6/1993 | |
| JP | 06-056884 A | 3/1994 | |
| JP | 07-177896 A | 7/1995 | |
| WO | 03/035674 A1 | 5/2003 | |
| WO | 2008/047792 A1 | 4/2008 | |

OTHER PUBLICATIONS

Deneke et al. "Regulation of cellular glutathione" Am J Physiol. Oct. 1989;257(4 Pt 1):L163-73.*
Japanese Patent Office, International Search Report in International Patent Application No. PCT/JP2011/059776 (Jul. 12, 2011) English translation.
Jelsch et al., "The Oxidized Form of Glutathione," *Acta Crystallographica Section C*, 55: 1538-1540 (1999).
European Patent Office, Extended European Search Report in European Patent Application No. 11772056.5 (Jan. 2, 2014).

* cited by examiner

*Primary Examiner* — Christina Bradley
(74) *Attorney, Agent, or Firm* — Leydig, Voit & Mayer, Ltd.

(57) ABSTRACT

Provided is a novel crystal of oxidized glutathione hexahydrate. Crystal of oxidized glutathione hexahydrate is produced by cooling an aqueous solution containing oxidized glutathione to 15° C. or lower to precipitate a crystal of oxidized glutathione hexahydrate.

8 Claims, No Drawings

… … … … …

CRYSTALLINE OXIDIZED GLUTATHIONE AND PRODUCTION METHOD THEREFOR

CROSS-REFERENCE TO RELATED APPLICATIONS

This patent application is the U.S. national phase of International Patent Application PCT/JP2011/059776, filed on Apr. 21, 2011, which claims the benefit of Japanese Patent Application No. 2010-097529, filed on Apr. 21, 2010, which are incorporated by reference in their entireties herein.

TECHNICAL FIELD

The present invention relates to a crystal of oxidized glutathione useful as a product, raw material, intermediate or the like of health-aid food, pharmaceuticals, cosmetics or the like, and a process for producing the crystal.

BACKGROUND ART

Oxidized glutathione has the same actions as reduced glutathione, and as actions of oxidized glutathione, for example, hepatic detoxification action via oral administration, and the like are known (Non-Patent Document 1). Due to this, oxidized glutathione may be used for various applications in which reduced glutathione has been used, and is useful, for example, as a product, raw material or intermediate of health-aid food, pharmaceuticals, cosmetics, and the like.

Known process for producing oxidized glutathione include a process in which an aqueous solution or yeast extract solution containing oxidized glutathione obtained by a fermentation process, enzymatic process or the like is used as a starting material, and in the aqueous solution or yeast extract solution, the reduced glutathione is converted into the oxidized glutathione to obtain a solution of oxidized glutathione, and then by conducting a concentration, a dilution and the like, an aqueous solution or yeast extract solution containing the oxidized glutathione is obtained (Patent Documents 1 and 2); a method for obtaining powder of yeast extract solution containing oxidized glutathione by adding excipients and the like, and freeze-drying, spray-drying or the like (Patent Document 2); a process for producing a crystal of oxidized glutathione monohydrate by adding alcohol and the like dropwise to an aqueous solution containing oxidized glutathione (Patent Document 3); a process for producing a crystal of oxidized glutathione octahydrate (Non-Patent document 2) and the like.

However, it is known that the production method by freeze-drying a solution of oxidized glutathione shows poor impurity selectivity and require a large amount of energy for freeze-drying so that it is not suitable for industrialization. Meanwhile, the method based on spray-drying is known to show an increase in impurities due to thermal contact.

In addition, it is known that the crystal of oxidized glutathione octahydrate is problematic in that the content of water contained in the crystal is not uniform, and shows poor stability and a long time up to 3-4 days is required to obtain the crystal, and that the crystal of oxidized glutathione monohydrate leave room for improvement in that crystal separation capability is poor because it is a needle-like crystal and easily agglomerate, impurity selectivity (purification ability) is poor and crystal growth rate is slow.

Therefore, there is a need for a crystal of oxidized glutathione that has excellent stability and is handled industrially with ease.

PRIOR ART

Patent Document

[Patent Document 1] Japanese Patent Application Laid-Open No. Hei 5-146279
[Patent Document 2] Japanese Patent Application Laid-Open No. Hei 7-177896
[Patent Document 3] Japanese Patent No. 4401775

Non-Patent Document

[Non-Patent Document 1] J. Nutr. Sci., 44, pp613 (1998)
[Non-Patent Document 2] 1999 International Union of Crystallograpy, pp1538 (1999)

DISCLOSURE OF INVENTION

Problems to be Solved by the Invention

An object of the present invention is to provide a crystal of oxidized glutathione useful as a product, raw material, intermediate or the like of health-aid food, pharmaceuticals, cosmetics and the like, and to provide a process for producing a crystal of oxidized glutathione suitable for mass synthesis or industrialization.

Means for Solving the Problems

The present invention relates to the following (1) to (8).

(1) A crystal of oxidized glutathione hexahydrate.
(2) A crystal of oxidized glutathione hexahydrate having peaks at a diffraction angle ($2\theta$) of 8.12°, 9.70°, 10.62°, 12.44°, 14.20°, 16.22°, 16.38°, 17.90°, 18.90°, 19.52°, 20.26°, 21.32°, 21.60°, 22.82°, 23.34°, 24.40°, 24.72°, 24.98°, 25.56°, 26.18°, 26.68°, 27.20°, 28.32°, 29.00°, 29.66°, 31.02°, 31.58°, 32.20°, 32.72°, 32.88°, 34.48° and 41.56° in powder X-ray diffraction.
(3) A process for producing the crystal of oxidized glutathione hexahydrate according to (1) or (2), characterized by cooling an aqueous solution containing oxidized glutathione to 15° C. or lower to precipitate a crystal of oxidized glutathione hexahydrate and then collecting the crystal of oxidized glutathione hexahydrate from the aqueous solution.
(4) A process for producing the crystal of oxidized glutathione hexahydrate according to (1) or (2), characterized by comprising a step of adding or adding dropwise a solvent selected from the group consisting of alcohols and ketones to an aqueous solution containing oxidized glutathione at 15° C. or lower.
(5) A process for producing the crystal of oxidized glutathione hexahydrate according to (1) or (2), characterized by comprising a step of adding or adding dropwise a solvent selected from the group consisting of methanol, ethanol, n-propanol and isopropyl alcohol to an aqueous solution containing oxidized glutathione at 15° C. or lower.
(6) A process for producing the crystal of oxidized glutathione hexahydrate according to (1) or (2), characterized by comprising a step of adding or adding dropwise methanol to an aqueous solution containing oxidized glutathione at 15° C. or lower.
(7) The process according to any one of (3) to (6), wherein the aqueous solution containing oxidized glutathione is an aqueous solution obtained by treating a solution containing oxidized glutathione with a synthetic adsorbent resin or ion exchange resin.

(8) A crystal of oxidized glutathione hexahydrate obtained by the process according to any one of (3) to (7).

Effects of the Invention

According to the present invention, there are provided a crystal of oxidized glutathione useful as a product, raw material, intermediate or the like of health-aid food, pharmaceuticals, cosmetics and the like, and a process for producing the same.

EMBODIMENTS FOR CARRYING OUT THE INVENTION

In the present invention, the solution of oxidized glutathione may be any solution containing oxidized glutathione, but examples thereof may include an aqueous solution, culture solution, yeast extract solution, bacteriostatic solution and the like containing oxidized glutathione obtained by acquiring reduced glutathione prepared via a synthetic method, fermentation method or method of extraction from yeast, for example, according to a method described in Japanese Patent Publication No. Sho 44-239, Japanese Patent Publication No. Sho 46-4755, Japanese Patent Publication No. Sho 46-2838 or Japanese Patent Application Laid-Open No. Sho 61-74595, as a reaction solution containing reduced glutathione as it is, or, for example, as a purified solution, freeze-dried powder or the like, and oxidizing the acquired reduced glutathione with, for example, oxygen, hydrogen peroxide, enzyme capable of oxidizing ascorbic acid or the like according to a method described in Japanese Patent Application Laid-Open No. Hei 5-146279 or Japanese Patent Application Laid-Open No. Hei 7-177896.

Although the aqueous solution containing oxidized glutathione may be any aqueous solution containing oxidized glutathione, an aqueous solution having a purity of oxidized glutathione in dissolved components of 50% or higher is preferred and an aqueous solution having a purity of 70% or higher is more preferred. The aqueous solution may contain other organic solvents, including alcohols such as methanol, ethanol, isopropyl alcohol, n-propanol and the like, and ketones such as acetone, methyl ethyl ketone and the like. The aqueous solution preferably has a water content of 20% or higher. Particularly, examples thereof may include an aqueous solution prepared, for example, by pretreatment of a solution of oxidized glutathione (this solution of oxidized glutathione has the same meaning as the above-defined solution of oxidized glutathione).

The pretreatment method may include membrane treatment, gel filtration treatment, active carbon treatment, ion exchange resin treatment, synthetic adsorbent resin treatment, chelate resin treatment, solvent precipitation and the like, preferably active carbon treatment, ion exchange resin treatment, synthetic adsorbent resin treatment, solvent precipitation and the like, and among them, synthetic adsorbent resin treatment or ion exchange resin treatment is more preferred, and such treatments may be used in combination as appropriate.

In addition, the aqueous solution containing oxidized glutathione is preferably an aqueous solution having a concentration of oxidized glutathione contained therein of 50 to 700 g/L. Particularly, an aqueous solution having a concentration of 100 to 400 g/L is preferred, and such solutions are prepared suitably, for example, by concentration and the like.

As a water miscible organic solvent, any organic solvents miscible with water may be used, but preferred examples thereof include alcohols, such as methanol, ethanol, isopropyl alcohol, n-propanol and the like, and ketones, such as acetone, methyl ethyl ketone and the like.

As a synthetic adsorbent resin, for example, a nonpolar porous adsorbent resin or the like may be used, and particular examples thereof may include Diaion HP series (for example, HP10, HP20, HP21, HP30, HP40, HP50 and the like, manufactured by Mitsubishi Chemical Corporation), Diaion SP800 series (for example, SP800, SP825, SP850, SP875 and the like, manufactured by Mitsubishi Chemical Corporation), Diaion SP200 series (for example, SP205, SP206, SP207, SP207SS and the like, manufactured by Mitsubishi Chemical Corporation), AMBERLITE XAD series (for example, XAD4, XAD7HP, XAD 16, XAD 1600 and the like, manufactured by Rhom and Hass Company), and the like. Among them, SP207 is preferred.

An ion exchange resin may include a strongly basic anion exchange resin, a weakly basic anion exchange resin, a strongly acidic cation exchange resin, a weakly acidic cation exchange resin and the like.

Examples of a strongly basic anion exchange resin may include Diaion PA series (for example, PA306, PA312, PA412 and the like, manufactured by Mitsubishi Chemical Corporation) and the like, and examples of a weakly basic anion exchange resin may include Diaion WA series (for example, WA10, WA20, WA30 and the like, manufactured by Mitsubishi Chemical Corporation) and the like.

Examples of a strongly acidic cation exchange resin may include AMBERLITE IR series (for example, 124 Na, 252 Na and the like, manufactured by Organo Corporation), Dowex (for example, XUS-40232.01 and the like, manufactured by Dow Chemical Company) and the like, and examples of a weakly acidic cation exchange resin may include AMBERLITE IRC series (for example, IRC-50, IRC-70 and the like, manufactured by Rhom and Hass Company) and the like.

Next, an embodiment of a process for producing a crystal of oxidized glutathione hexahydrate will be described in detail.

1. Preparation of Aqueous Solution Containing Oxidized Glutathione

According to the method described in Japanese Patent Application Laid-Open No. Hei 5-146279, or Japanese Patent Application Laid-Open No. Hei 7-177896, reduced glutathione is oxidized, for example, with oxygen, hydrogen peroxide, enzyme capable of oxidizing ascorbic acid or the like to obtain an aqueous solution, culture solution, yeast extract solution, bacteriostatic solution or the like, containing oxidized glutathione. This may be subjected optionally to pretreatment such that a purity of oxidized glutathione in dissolved components may be 50% or higher, preferably 70% or higher.

The pretreated solution or untreated solution is concentrated to a concentration of oxidized glutathione contained therein of 50 to 700 g/L, preferably 100 to 400 g/L, thereby obtaining an aqueous solution containing oxidized glutathione. In addition, the aqueous solution containing oxidized glutathione may also be obtained by freeze-drying the pretreated solution or untreated solution to obtain powder, and dissolving the powder in water to the same concentration as mentioned above. Herein, oxidized glutathione commercially available as powder may also be used.

A pretreatment method for obtaining an aqueous solution containing oxidized glutathione may include membrane treatment, gel filtration treatment, active carbon treatment, ion exchange resin treatment, synthetic adsorbent resin treatment, chelate resin treatment (examples of a chelate resin used for chelate resin treatment include Duolite C 467 manufactured by Sumitomo Chemical Co., Ltd., and the like), solvent precipitation and the like, preferably active carbon treatment, ion exchange resin treatment, synthetic adsorbent resin treatment, solvent precipitation and the like, and among them, synthetic adsorbent resin treatment or ion exchange resin treatment is more preferred, and such treatments may be used in combination as appropriate.

More particularly, for example, an aqueous solution, culture solution, yeast extract solution, bacteriostatic solution or the like, containing oxidized glutathione, may be loaded to a synthetic adsorbent resin, preferably SP207, and subjected to separation and purification using, as an eluent, water or a water miscible organic solvent (the water miscible organic solvent has the same meaning as defined above) alone or in combination of two or more, or an aqueous solution, culture solution, yeast extract solution, bacteriostatic solution or the like, containing oxidized glutathione, may be loaded to a strongly acidic cation exchange resin ($H^+$ type) having a crosslinking degree of 12% or more, preferably SK112 or SK116, and then loaded to a strongly acidic cation exchange resin ($H^+$ type) having a crosslinking degree of 4% or less, preferably SK102 or XUS-40232.01, and subjected to separation and purification by elution with an eluent which is mixed with water or a water miscible organic solvent (the water miscible organic solvent has the same meaning as defined above) alone or in combination of two or more, aqueous ammonia solution, aqueous sodium chloride solution or the like, thereby obtaining an aqueous solution containing oxidized glutathione having high purity.

As the starting reduced glutathione, a commercially available product or an aqueous solution, purified solution or freeze-dried powder containing reduced glutathione obtained by a synthetic method, fermentation method or yeast extraction method according to a known method (for example, a method described in Japanese Patent Publication No. Sho44-239, Japanese Patent Publication No. Sho46-4755, Japanese Patent Publication No. Sho46-2838 or Japanese Patent Application Laid-Open No. Sho61-74595 or the like) may be used.

2. Production of Crystal of Oxidized Glutathione Hexahydrate

The aqueous solution containing oxidized glutathione obtained from 1. is adjusted to a pH of 2.5 to 3.5 with hydrochloric acid or sulfuric acid or aqueous solution of sodium hydroxide or the like as necessary, and then the aqueous solution is allowed to stand or is stirred at a temperature of −20 to 15° C., preferably 0 to 10° C., for 1 minute to 48 hours, more preferably 1 to 24 hours to perform cooling crystallization. In addition, crystallization may be carried out by cooling to the corresponding temperature over 1 minute to 48 hours, preferably 1 to 24 hours.

In addition, when carrying out cooling crystallization, a solvent selected from alcohols and ketones may be added or added dropwise to the aqueous solution containing oxidized glutathione, thereby precipitating a crystal of oxidized glutathione hexahydrate.

Examples of alcohol solvents include ethanol, propanol, n-propanol, isopropyl alcohol and the like, and examples of ketone solvents include acetone, methyl ethyl ketone and the like.

The solvent may be added in an amount of 0.1 to 100 times, preferably 0.1 to 10 times, and more preferably 0.1 to 3 times of the aqueous solution containing oxidized glutathione. In addition, when adding dropwise the solvent, the above-defined amount of solvent may be added dropwise over 1 minute to 10 hours, preferably 1 to 7 hours.

When carrying out cooling crystallization, whether or not the solvent is added or added dropwise, a seed crystal may be added as necessary. The seed crystal may be added at a concentration of 0.001 to 50 g/L, preferably 0.01 to 5 g/L, and when added dropwise, they may be added dropwise until the final concentration becomes the above-defined concentration.

The precipitated crystal is separated, for example, by centrifugal filtration, decantation or the like, washed with water or a water miscible organic solvent, and then the obtained crystal is dried under reduced pressure or ventilation, thereby obtaining a crystal of oxidized glutathione hexahydrate. In addition, the crystal may be further purified by further operation such as washing, drying, recrystallization and the like.

The crystal of oxidized glutathione hexahydrate obtained by the above-described method may be obtained as an adduct with various water miscible organic solvents, but such an adduct with various water miscible organic solvents is also included in the crystal of the present application.

In addition, there is a case where crystals having a different crystal type or a different particle size may be present in the crystal of oxidized glutathione hexahydrate obtained by the above method, and they may be obtained alone or in a mixture, but such crystals having a different crystal type or particle size alone or in a mixture are also included in the crystal of the present application.

Hereinafter, the preservation stability (hygroscopic property) of the crystal of oxidized glutathione according to the present invention will be described in detail with reference to Test Example.

Test Example: Comparison between Crystal of Oxidized Glutathione Hexahydrate and Freeze-Dried Powder of Oxidized Glutathione in Hygroscopic Property The hygroscopic properties for the crystal of oxidized glutathione hexahydrate obtained from Example 3 and the freeze-dried powder of oxidized glutathione obtained from Reference Example 1 were traced under the conditions of 23° C., ambient pressure and a humidity of 70%. As a result, the freeze-dried powder of oxidized glutathione obtained from Reference Example 1 markedly absorbed moisture, and was deliquesced after 2 days. On the contrary, the crystal of oxidized glutathione hexahydrate obtained from Example 3 showed little change in water content, and was found to be very stable.

Example 1

Production of Crystal of Oxidized Glutathione Hexahydrate (1)

The freeze-dried powder (3.0 g) of oxidized glutathione obtained from Reference Example 1 was dissolved in water to provide an aqueous solution containing oxidized glutathione (30 mL, concentration of oxidized glutathione: 100 g/L). The aqueous solution was allowed to stand at 5° C. for 48 hours to precipitate a crystal. The precipitated crystal was separated by filtration and dried under ventilation to obtain the crystal (1.0 g) of oxidized glutathione hexahydrate. In addition, single crystal X-ray structural analysis showed that the crystal is provided as hexahydrate.

Hereinafter, physicochemical properties of the obtained oxidized glutathione hexahydrate will be described.

Hydration number: hexahydrate

Melting point: 191° C.

Powder X-Ray Diffraction [diffraction angle)(2θ°, the number in a parenthesis indicates a relative intensity ratio ($I/I_0$)]: 8.12° (100), 9.70° (33), 10.62° (43), 12.44° (14), 14.20° (13), 16.22° (71), 16.38° (22), 17.90° (18), 18.90° (9), 19.52° (76), 20.26° (17), 21.32° (13), 21.60° (22), 22.82° (41), 23.34° (26), 24.40° (34), 24.72° (23), 24.98° (33), 25.56° (12), 26.18° (18), 26.68° (34), 27.20° (9), 28.32° (12), 29.00° (13), 29.66° (11), 31.02° (10), 31.58° (10), 32.20° (9), 32.72° (11), 32.88° (12), 34.48° (18) and 41.56° (13).

The following Table 1 shows the results of comparison between the saturation solubility of the crystal of oxidized glutathione hexahydrate obtained as described above and that of oxidized glutathione monohydrate.

TABLE 1

| Saturation solubility of the crystal of oxidized glutathione hexahydrate | |
|---|---|
| | Saturation solubility (g/L) <$H_2O$, 30° C.> |
| oxidized glutathione hexahydrate | 173 |
| oxidized glutathione monohydrate | 13.5 |

Example 2

Production of Crystals of Oxidized Glutathione Hexahydrate (2)

The freeze-dried powder (10.0 g) of oxidized glutathione obtained from Reference Example 1 was dissolved in water to provide an aqueous solution containing oxidized glutathione (33 mL, concentration of oxidized glutathione: 300 g/L). The aqueous solution was cooled to 5° C., and the crystal (0.1 g) obtained from Examples 1 was added thereto as a seed crystal. To the resultant solution, methanol (66 mL) was added over 5 hours to perform crystallization. The crystallization solution was aged for 1 hour, and the precipitated crystal was separated by filtration, and dried under ventilation to obtain the crystal (8.5 g) of oxidized glutathione hexahydrate.

Example 3

Production of Crystal of Oxidized Glutathione (3)

An aqueous solution containing reduced glutathione obtained according to the method described in Example 2 of Japanese Patent Application Laid-Open No. Sho61-74595 was adjusted to pH 7.5 with an aqueous sodium hydroxide solution according to the method described in Japanese Patent Application Laid-Open No. Hei 5-146279, and then oxygen was blown into the system to perform oxidation, thereby obtaining an aqueous solution containing oxidized glutathione (48.1 L, concentration of oxidized glutathione: 18.0 g/L).

This aqueous solution was adjusted to pH 3.0 with sulfuric acid, and subjected to bacteriostatic treatment to obtain a bacteriostatic solution of oxidized glutathione (55.5 L, concentration of oxidized glutathione: 14.4 g/L). The bacteriostatic solution was loaded to Diaion SK116 (22 L) and then, loaded to Dowex XUS-40232.01 (13 L) to perform adsorption of oxidized glutathione, thereby eluting the oxidized glutathione with an aqueous ammonia solution (20 L, concentration: 2 mol/L).

This eluate was loaded to SK116 (7 L) to make a free form and to remove ammonia, thereby obtaining an aqueous solution containing oxidized glutathione (19 L, concentration of oxidized glutathione: 35.4 g/L). To the aqueous solution, active carbon (130 g) was added, followed by stirring at 40° C. for 1 hour, and then active carbon was removed by filtration. The obtained filtrate was concentrated to 2.24 L (concentration of oxidized glutathione: 300 g/L), and cooled to 5° C.

To the concentrate, the crystal (13 g) obtained by the method described in Example 1 was added as a seed crystal, and methanol (4.6 L) was added over 5 hours to perform crystallization. The precipitated crystal was separated by filtration, and dried under ventilation to obtain the crystal (610 g) of oxidized glutathione hexahydrate.

Reference Example 1

Acquisition of Freeze-Dried Powder of Oxidized Glutathione

After 4.8 g of reduced glutathione obtained by the method described in Japanese Patent Application Laid-Open No. Hei 5-146279 was dissolved in water (24 mL), the obtained aqueous solution containing reduced glutathione was adjusted to pH 7.5 with an aqueous sodium hydroxide solution, and stirred in the presence of copper sulfate. The reaction mixture was loaded to Diaion SK116 (32 mL) and Duolite C467 (4 ml, Sumitomo Chemical Co. Ltd.), and the treated solution was concentrated to obtain an aqueous solution containing oxidized glutathione (11 mL, concentration of oxidized glutathione 300 g/L). The aqueous solution was freeze-dried to obtain 3.0 g of freeze-dried powder of oxidized glutathione.

INDUSTRIAL APPLICABILITY

According to the present invention, there are provided a crystal of oxidized glutathione useful as a product, raw material, intermediate or the like of health-aid food, pharmaceuticals, cosmetics or the like, and a process for producing a crystal of oxidized glutathione suitable for mass synthesis or industrialization.

The invention claimed is:

1. A process for producing a crystal of oxidized glutathione hexahydrate having peaks at a diffraction angle (2θ) of 8.12°, 9.70°, 10.62°, 12.44°, 14.20°, 16.22°, 16.38°, 17.90°, 18.90°, 19.52°, 20.26°, 21.32°, 21.60°, 22.82°, 23.34°, 24.40°, 24.72°, 24.98°, 25.56°, 26.18°, 26.68°, 27.20°, 28.32°, 29.00°, 29.66°, 31.02°, 31.58°, 32.20°, 32.72°, 32.88°, 34.48° and 41.56° in powder X-ray diffraction comprising cooling an aqueous solution containing oxidized glutathione to 15° C. or lower to precipitate a crystal of oxidized glutathione hexahydrate, and then collecting the crystal of oxidized glutathione hexahydrate from the aqueous solution.

2. The process according to claim 1, wherein the aqueous solution containing oxidized glutathione is an aqueous solution obtained by treating a solution containing oxidized glutathione with a synthetic adsorbent resin or ion exchange resin.

3. A process for producing a crystal of oxidized glutathione hexahydrate having peaks at a diffraction angle (2θ) of 8.12°, 9.70°, 10.62°, 12.44°, 14.20°, 16.22°, 16.38°, 17.90°, 18.90°, 19.52°, 20.26°, 21.32°, 21.60°, 22.82°, 23.34°, 24.40°, 24.72°, 24.98°, 25.56°, 26.18°, 26.68°, 27.20°, 28.32°, 29.00°, 29.66°, 31.02°, 31.58°, 32.20°, 32.72°, 32.88°, 34.48° and 41.56° in powder X-ray diffraction comprising adding or adding dropwise a solvent selected from the group consisting of alcohols and ketones to an aqueous solution containing oxidized glutathione at 15° C. or lower.

4. The process according to claim 3, wherein the aqueous solution containing oxidized glutathione is an aqueous solution obtained by treating a solution containing oxidized glutathione with a synthetic adsorbent resin or ion exchange resin.

5. A process for producing a crystal of oxidized glutathione hexahydrate having peaks at a diffraction angle (2θ) of 8.12°, 9.70°, 10.62°, 12.44°, 14.20°, 16.22°, 16.38°, 17.90°, 18.90°, 19.52°, 20.26°, 21.32°, 21.60°, 22.82°, 23.34°, 24.40°, 24.72°, 24.98°, 25.56°, 26.18°, 26.68°, 27.20°, 28.32°, 29.00°, 29.66°, 31.02°, 31.58°, 32.20°, 32.72°, 32.88°, 34.48° and 41.56° in powder X-ray diffraction comprising adding or adding dropwise a solvent selected from the group consisting of methanol, ethanol, n-propanol and isopropyl alcohol to an aqueous solution containing oxidized glutathione at 15° C. or lower.

6. The process according to claim 5, wherein the aqueous solution containing oxidized glutathione is an aqueous solution obtained by treating a solution containing oxidized glutathione with a synthetic adsorbent resin or ion exchange resin.

7. A process for producing a crystal of oxidized glutathione hexahydrate having peaks at a diffraction angle (2θ) of 8.12°, 9.70°, 10.62°, 12.44°, 14.20°, 16.22°, 16.38°, 17.90°, 18.90°, 19.52°, 20.26°, 21.32°, 21.60°, 22.82°, 23.34°, 24.40°, 24.72°, 24.98°, 25.56°, 26.18°, 26.68°, 27.20°, 28.32°, 29.00°, 29.66°, 31.02°, 31.58°, 32.20°, 32.72°, 32.88°, 34.48° and 41.56° in powder X-ray diffraction comprising adding or adding dropwise methanol to an aqueous solution containing oxidized glutathione at 15° C. or lower.

8. The process according to claim 7, wherein the aqueous solution containing oxidized glutathione is an aqueous solution obtained by treating a solution containing oxidized glutathione with a synthetic adsorbent resin or ion exchange resin.

* * * * *